United States Patent [19]
Hassler et al.

[11] Patent Number: 5,031,626
[45] Date of Patent: Jul. 16, 1991

[54] EXTRACORPOREAL LITHOTRIPSY APPARATUS WITH AN ULTRASOUND LOCATING SYSTEM

[75] Inventors: Dietrich Hassler, Uttenreuth; Erhard Schmidt, Erlangen, both of Fed. Rep. of Germany

[73] Assignee: Siemens Aktiengesellschaft, Munich, Fed. Rep. of Germany

[21] Appl. No.: 392,352

[22] Filed: Aug. 11, 1989

[30] Foreign Application Priority Data

Aug. 17, 1988 [EP] European Pat. Off. .......... 8811360.7

[51] Int. Cl.$^5$ ............................................. A61B 17/22
[52] U.S. Cl. ........................... 128/660.03; 128/24 EL
[58] Field of Search ......... 128/24 EL, 660.03, 660.07, 128/660.1, 662.03

[56] References Cited

U.S. PATENT DOCUMENTS

| | | |
|---|---|---|
| 4,030,344 | 6/1977 | Northeved et al. . |
| 4,034,744 | 7/1977 | Goldberg . |
| 4,328,707 | 5/1982 | Clement et al. . |
| 4,589,284 | 5/1986 | Breimesser et al. . |
| 4,617,931 | 10/1986 | Dory . |
| 4,674,505 | 6/1987 | Pauli et al. . |
| 4,844,079 | 7/1989 | Naser et al. . |

FOREIGN PATENT DOCUMENTS

| | | |
|---|---|---|
| 0097917 | 1/1984 | European Pat. Off. . |
| 0142862 | 5/1985 | European Pat. Off. . |
| 0278303 | 8/1988 | European Pat. Off. . |
| 2719130 | 1/1978 | Fed. Rep. of Germany . |
| 2722252 | 11/1978 | Fed. Rep. of Germany . |
| 3736733 | 5/1988 | Fed. Rep. of Germany ... 128/24 EL |
| 2608913 | 7/1988 | France . |

*Primary Examiner*—Ruth S. Smith
*Attorney, Agent, or Firm*—Hill, Van Santen, Steadman & Simpson

[57] ABSTRACT

An extracorporeal lithotripsy apparatus for treating a calculus in the body of a patient has a shock wave source which generates shock waves converging in a focus zone, and an ultrasound locating system having a sector applicator with which at least the focus zone can be scanned. The sector applicator includes a number of ultrasound transducers, so that a number of layers, proceeding parallel to each other, can be quasi-simultaneously scanned. The number of layers which can be scanned corresponds to the number of ultrasound transducers. The layers are directly adjacent each other so that displacement of a calculus in the body during treatment in a direction transverse to the acoustic axes of the scanned sectors can be observed.

19 Claims, 3 Drawing Sheets

EXTRACORPOREAL LITHOTRIPSY APPARATUS WITH AN ULTRASOUND LOCATING SYSTEM

BACKGROUND OF THE INVENTION

1. Field of the Invention

The present invention is directed to an extracorporeal lithotripsy apparatus for treating a calculus in a patient, and in particular to such an apparatus having an ultrasound locating system for identifying the location of the calculus within the patient.

1. Description of the Prior Art

The treatment of calculus ailments by means of an extracorporeal lithotripsy apparatus requires some means, such an ultrasound locating system, for correctly positioning the lithotripsy apparatus and the patient relative to each other so that the calculus, such as a kidney stone, is located in the focus of the shock waves. The focused shock waves are then coupled into the body of the patient, and act on the calculus to disintegrate it into fragments which can be naturally eliminated (excreted).

An installation of this type is described in European application 0 148 653, corresponding to U.S. Pat. No. 4,617,931. In this known installation, a layer of the body of the patient to be treated, which contains the acoustic axis of the shock wave source, is scanned by a B-scan applicator to locate the calculus to be disintegrated. If, during the treatment, the calculus migrates out of the body layer which is scannable by the B-scan applicator, such as due to respiration of the patient or due to the effect of the shock waves, the calculus will no longer be visible in the continuous display. Even if measures are provided which permit adjustment of the sector applicator so that the center plane of the scannable layer coincides with the principles direction of displacement of the calculus. This is because, if the calculus has moved, there is no way to determine on which side of the scannable layer the calculus is disposed after movement. The calculus must therefore be searched for blindly. This is time consuming and makes the entire treatment more difficult.

It has been suggested to provide a second sector applicator with which a second body layer, also containing the acoustic axis of the shock wave source, can be scanned which, in combination with the first body layer, subtends an angle. Although additional information is received by this measure, it is only useful if the calculus moves by a small amount in the area of the focus zone.

SUMMARY OF THE INVENTION

It is an object of the present invention to provide an extracorporeal lithotripsy apparatus with an ultrasound locating system wherein displacement of a calculus to be disintegrated can be identified, so that the apparatus and/or the patient can be repositioned, in a simple and relatively rapid manner.

The above object is achieved in accordance with the principles of the present invention in an extracorporeal lithotripsy apparatus including an ultrasound locating system having a sector applicator which includes several ultrasound transducers. A number of layers of the patient, corresponding to the number of ultrasound transducers, which proceed parallel to each other can be scanned quasi-simultaneously. The sectors scanned by the respective transducers are directly adjacent to each other in the area of the focus zone. It is thus possible to reliably recognize relatively large displacements of the calculus, because the calculus, after leaving one of the scanned layers, enters directly into the adjacent layer, and is thus displayed continuously, so that identification can be made of which direction the calculus is moving. This means that the position of the lithotripsy apparatus and/or the patient relative to each other can immediately be re-adjusted, such as by tilting or tipping the apparatus so that the calculus is relocated in the focus zone or the center scanning plane. Preferably the scanned layers proceed approximately parallel to the acoustic axis of the shock wave source, on which the focus zone of the shock waves lies.

In a preferred embodiment of the invention, the shock wave source has an acoustic axis proceeding through the focus zone, and the sector applicator is a B-scan applicator containing an odd number of ultrasound transducers. The transducers are arranged such that the center scannable layer contains the acoustic axis of the shock wave source. If the calculus to be shattered is first disposed in the center layers, the side of the sector at which at the calculus moves out of the sector can be easily identified. Preferably, the ultrasound transducers are arranged relative to each other so that the center planes of the scannable layers proceed parallel to each other, so that even if the shock wave source has an adjustable focus distance, it is always insured that those sections of the layers which are located in the area of the focus zone are directly adjacent to each other. Particularly in shock wave sources having a fixed focus distance, it may also be provided that the ultrasound transducers are arranged relative to each other so that the respective center planes of the scannable layers diverge in the direction leading to the focus zone. The divergency of the center plane is selected in dependence on the location of the focus zone, so that those sections of the layers which are located in the area of the focus zone are directly adjacent to each other. In contrast to the arrangement of the transducers wherein the center planes of the scannable layers proceed parallel to each other, which requires the ultrasound transducers to be arranged laterally offset from each other. Such offsetting is required to a slight extent, and may not even be required at all, in the embodiment wherein the center planes of the scannable layer diverge in the direction leading to the focus zone. A coordinated tipping is sufficient, so that a space-saving structure of the B-scan applicator is possible.

It is also possible to use ultrasound transducers in the form of a phased-array, and to perform scanning of the layers in an electronic manner. It is, however, possible to construct the B-scan applicator with several ultrasound transducers in a particularly economical, simple and space-saving manner. This can be accomplished using a mechanical sector-scanner with the ultrasound transducers, either in the form of individual transducers or transducer-arrays with natural, mechanical or electronic focusing, attached to a rotor. The rotor is rotatable around an axle by a drive unit, with ultrasound transducers attached to the rotor at an angle offset to each other. The drive unit may be disposed on that side of the shock wave source facing away from the focus zone, with a driving connection being made from the drive unit to the rotor extending through a central opening in the shock wave source. This avoided reducing the aperture of the shock wave source due to the presence of the drive unit.

In another embodiment, the ultrasound locating system includes control electronics which permit the ultrasound B-images of the layers which are scannable by the sector applicator to be generated and displayed at the time. It is thus particularly easy for operating personnel to recognize movements of the calculus to be disintegrated from the B-images which are simultaneously displayed. Any mid-treatment adjustments which must be made can then be easily undertaken.

DESCRIPTION OF THE PREFERRED EMBODIMENTS

Figure 1:
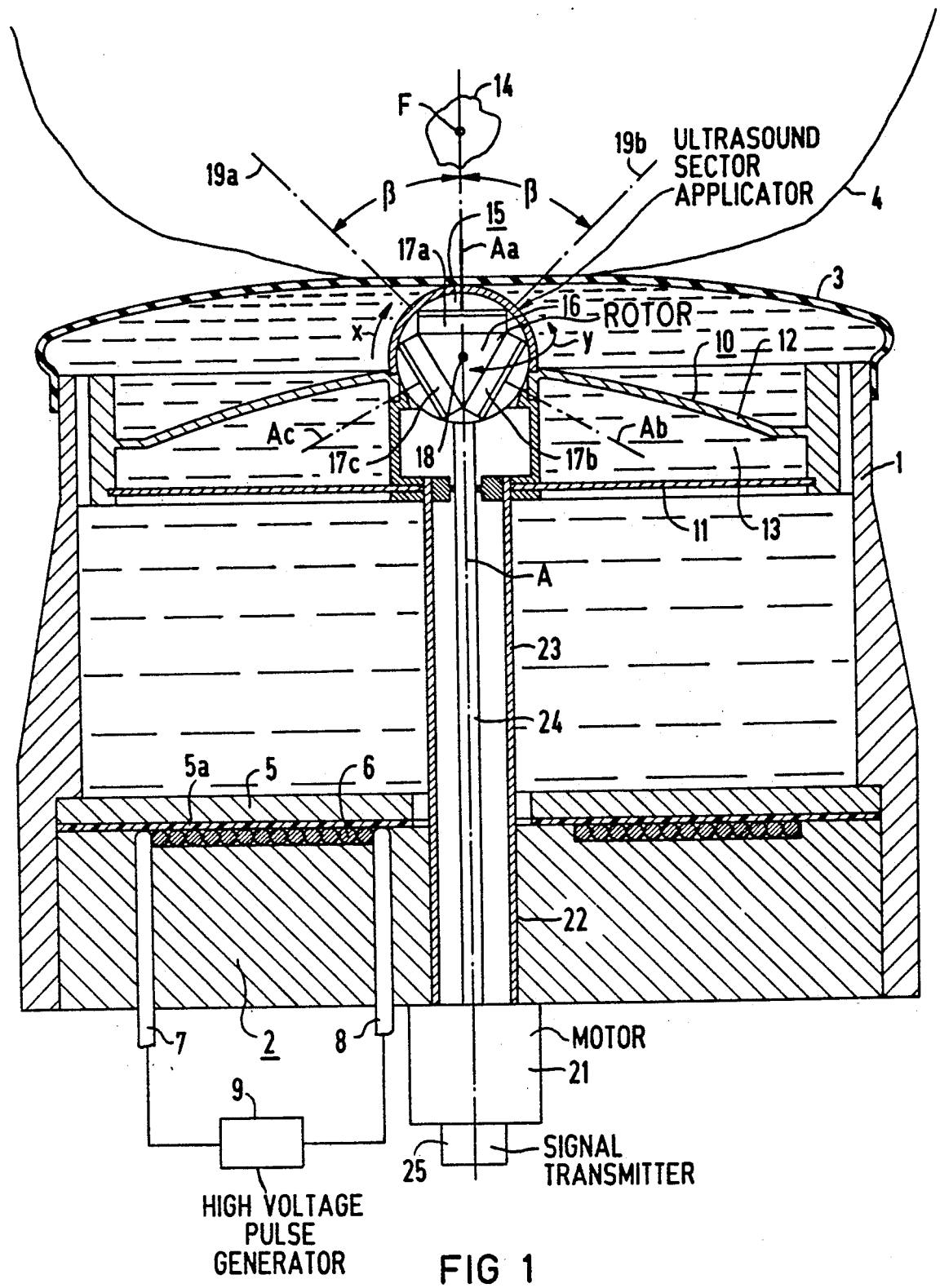
FIG. 1 is a side section view of an extracorporeal lithotripsy apparatus constructed in accordance with the principles of the present invention.

A first embodiment of an extracorporeal lithotripsy apparatus constructed in accordance with the principles of the present invention is shown in FIG. 1. The apparatus includes a substantially tubular housing 1, with a shock wave generator generally referenced 2 disposed at one end. At the opposite end, the housing 1 is closed by a flexible bellows 3, which functions to permit pressing of the apparatus against the body 4 of a patient in which a calculus 14 to be treated is disposed. The interior of the housing 1 is filled with a shock wave propagating medium, such as water, and the bellows 3 permits coupling of the shock waves into the body of the patient.

The shock wave generator 2 is an electro-dynamic shock wave generator, as described in detail in German OS 33 28 051. The shock wave generator 2 has a planar circular membrane 5 consisting of electrically conductive material. One side of the membrane 5 is in contact with the propagation medium in the housing 1, and the opposite side of the membrane 5 is covered by an insulating layer 5a. A planar coil 6 with spiral windings is disposed on the same side of the membrane 5, with the insulating 5a therebetween. The coil 6 is connected via terminals 7 and 8 to a high voltage pulse generator 9, by means of which the coil 6 is charged with high voltage pulses. When the coil 6 is charged with a high voltage pulse, the membrane 5 abruptly moves away from the coil 6 due to the effect of the magnetic field generated by the coil 6. As a result of this movement of the membrane 5, a pressure pulse is introduced into the propagation medium in the interior of the housing 1, and as it passes through the propagation medium, it is transformed into a shock wave. For simplicity, the term shock wave will be used exclusively herein, and will encompass the incipient shock waves in the form of pressure pulses. The shock wave propagates in the direction of a center axis of the shock wave generator 2.

To disintegrate the calculus 14, the shock wave must be focused. For this purpose, an acoustic focusing lens 10 is disposed between the shock wave generator 2 and the bellows 3, within the propagation medium inside the housing 1. The acoustic focusing lens in the embodiment of FIG. 1 is a liquid lens. The focusing lens 10 has an entry face 11 and an exit face 12, between which a lens liquid 13 is contained. The lens liquid 13 has a speed of sound therein which is different from the speed of sound in the propagation medium in the housing 1 surrounding the focusing lens 10. If, as in the embodiment of FIG. 1, the lens liquid 13 has a speed of sound therein which is less than the speed of sound in the propagation medium such as water, the focusing lens 10 must be a plane-convex or bi-convex lens. In the embodiment of FIG. 1, a plane-convex spherical focusing lens is provided. The wave fronts which approach the entry face 11 are proceeding substantially parallel to the face 11, and then travel through the lens 10, whereby the shock wave is focused to a focus zone F. The shock wave generator 2 and the focusing lens 10 thereby form, in combination, a means for generating focused shock waves having an acoustic axis A coinciding with the center axis of the shock wave generator 2, and on which the focus zone F lies.

The entry face 11 of the focusing lens 10 may consist, for example, of polymethylpentene, (TPX), whereas the exit face 12 may consist of Teflon ® (polytetrafluoroethylene). The lens liquid 13 may be a fluorocarbon liquid, such as Flutec ® PP3, ( a liquid chlorofluorocarbon distributed by Kali-Chemie of the Federal Republic of Germany) or Fluorinert ® FC 75 (a perfluoridated chemically and thermally stable liquid distributed by 3M).

To permit adjustment of the apparatus and/or the body 4 of the patient receiving the treatment relative to each other so that the calculus 14 is located in the focus zone F of the shock waves, as shown in FIG. 1, an ultrasound sector applicator 15 is provided. In the embodiment of FIG. 1 the sector applicator 15 is a mechanical sector scanner which permits, in combination with control circuitry described below, the generation of ultrasound B-images. The sector applicator 15 is received in a chamber filled with liquid provided in the center of the focusing lens 10, and is thus disposed, in the direction of propagation of the shock waves, before the focus zone F.

The sector applicator 15 contains an odd number of ultrasound transducers, such as three ultrasound transducers 17a, 17b and 17c, attached to a rotor 16 at angles of 120°. The rotor 16 is rotatable around an axle 18 in the direction of the arrow x. The axle 18 intersects the acoustic axis A perpendicularly, so that the transducers 17a, 17b and 17c successively respectively scan one sector-shaped layer of the body 4 parallel to the plane of the drawing. All three sector-shaped layers have the same aperture angle indicated by dashed lines 19a and 19b in FIG. 1. The lines 19a and 19b both subtend the same angle $\beta$ with respect to the acoustic axis A. The ultrasound transducers 17a, 17b and 17c transmit, if driven appropriately, ultrasonic waves having respective center axes Aa, Ab and Ac, indicated by dot and dashed lines. In the drawing of FIG. 1, the center axis Aa is in the same plane disposed perpendicular to the drawing as is the acoustic axis A, however, the axes A and Aa are not identical.

Figure 2:
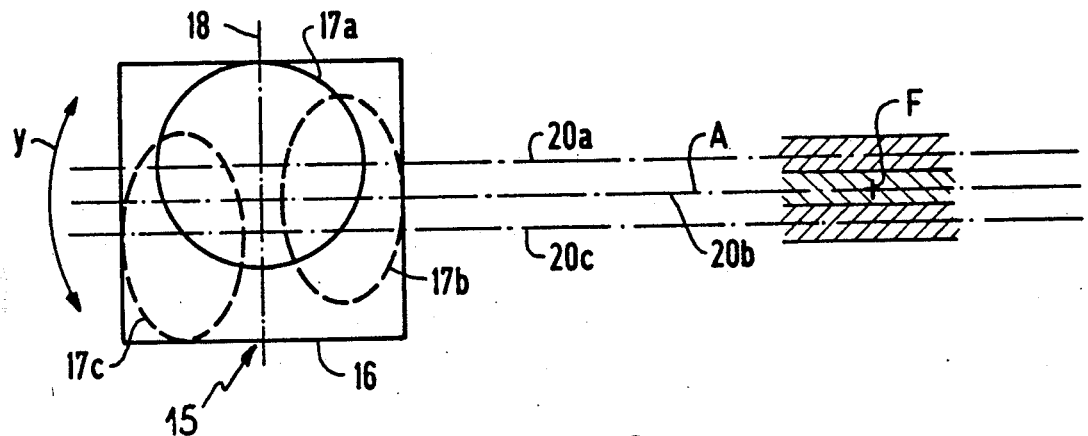
FIG. 2 is a schematic representation of certain components of the apparatus of FIG. 1 for explaining the operation of that apparatus.

As shown in the schematic illustration of FIG. 2, in which the focus zone F and the acoustic axis A are shown in side view, i.e., in a plane rotated by 90° with respect to the plane of the drawing of FIG. 1, the ultrasound transducers 17a, 17b and 17c are disposed on the rotor 16 laterally offset relative to each other in the direction of the axle 18, so that they scan different sector-shaped layers of the body 4 of the patient. The respective center planes 20a, 20b and 20c of these layers proceed exactly parallel to each other, and parallel to the acoustic axis A. The sections of those layers, in the region of the focus zone F, are shown cross-hatched in FIG. 2, from which it can be seen that the layers are directly adjacent to each other. The center plane 20b of the center layer, which is scannable by the ultrasound transducer 17b, contains the acoustic axis A. Each of the ultrasound transducers 17a, 17b and 17c respectively scans one sector-shaped layer, limited by the lines 19a and 19b shown in FIG. 1, with the bisector of each of these layers being in a common plane with the acoustic axis A.

Because the scannable layers have the same aperture angle, and because there bisectors lie in a common plane, a good compatibility of the information obtained from the scanning of each individual layer is insured. With respect to the propagation direction of the shock waves, the ultrasound transducers 17a, 17b and 17c are arranged before the focus zone F, and in the region of the acoustic axis A. This means that information can also be obtained regarding obstacles, such as ribs, which may be located in the propagation path of the shock waves.

An electric motor 21 is provided for driving the rotor 16, and is disposed on that side of the shock wave source 2 not facing the focus zone F, and behind the shock wave source 2. The shock wave source 2 has a central bore 22 therein, in which a tube 23 is provided with a liquid-tight seal at the exterior. The tube 23 extends in the direction of the focusing lens 10, and terminates in the chamber of the focusing lens 10 containing the sector applicator 15. In the interior of the tube 23, a driveshaft 24 is disposed for providing a power train from the motor 21 via a beveled gear arrangement, which is not shown in detail. In the tube 23, electrical lines are also provided, but are not shown in the drawing, for connecting the ultrasound transducer 17a, 17b and 17c to the electronic control circuitry described below. This connection is made, in the region of the transducers 17a, 17b and 17c, by a slip ring device, not shown in detail in the drawings but well known to those skilled in the art. The shaft 24 is guided into the chamber containing the sector applicator 15 in a liquid-tight fashion by a conical nipple. The motor 21 is provided with a signal transmitter 25 which generates and transmits electrical signals identifying the angular position of the rotor 16.

Figure 3:
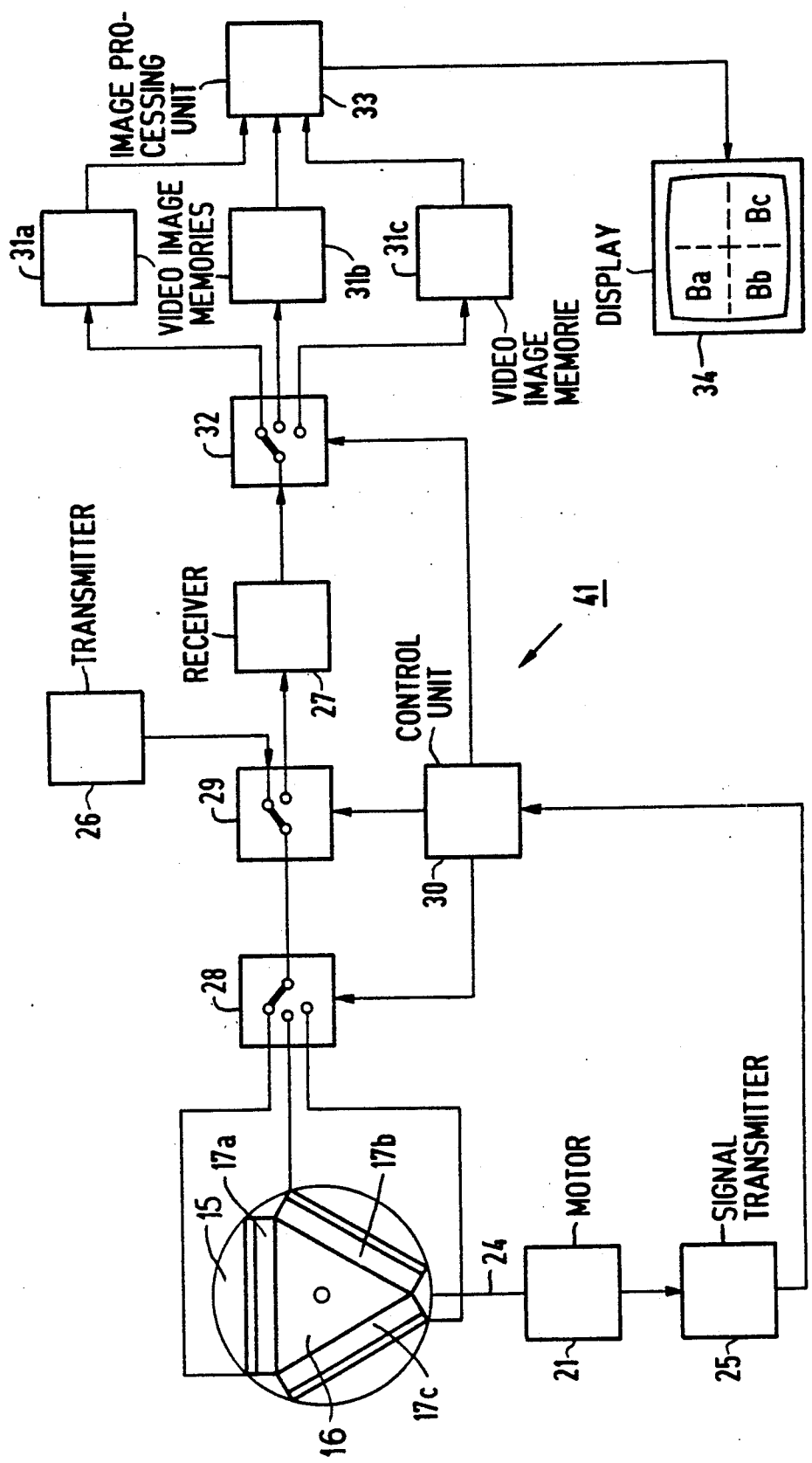
FIG. 3 is a schematic block diagram of a control circuit for operating the ultrasound transducer in the apparatus of FIG. 1.

A schematic illustration of the control circuitry for the sector applicator 15 is shown in FIG. 3. The sector applicator 15 is schematically illustrated with the ultrasound transducers 17a, 17b and 17c attached to the rotor 16 with the motor 21, the drive shaft 24 and the signal transmitter 25 also being schematically shown. In addition to the sector applicator 15, the ultrasound locating system includes control electronics, generally referenced 41. The control electronics 41 includes a transmitter 26 of known construction with which the transducers 17a, 17b and 17c of the sector applicator 15 can be driven to generate ultrasound, and a receiver 27 of known construction for receiving ultrasound echoes via the transducers 17a, 17b and 17c. The receiver 27 converts the ultrasound echoes into video signals.

A first switching stage 28 is provided by means of which one of the ultrasound transducers 17a, 17b or 17c can be selected. A second switching stage 29 is provided which connects the selected ultrasound transducer to either the transmitter 26 or the receiver 27. The first switching stage 28 is formed by a 3-to-1 analog multiplexer, which is shown in FIG. 3 as a three-pole, single-throw switch. The second switching stage 29 is formed by a 1-to-2 analog demultiplexer which is shown in FIG. 2 by a single pole, double throw switch. In combination, the states of the switching stages 28 and 29 define a connection of one of the ultrasound transducers to either the transmitter 26 or the receiver 27. The switching stages 28 and 29 are actuated by a control unit 30, in a manner described below.

A number of video image memories 31a, 31b and 31c are provided, corresponding in number to the number of ultrasound transducers, one of which can be connected to the output of the receiver 27 by a third switching stage 32. The video image memory which is connected to the output of the receiver 27 via the switching stage 32 stores the video signals from the output of the receiver 27, thereby overwriting data which may have previously been stored in that memory. The third switching stage 32 is a 1-to-3 demultiplexer which is also actuated by the control unit 30. The third switching stage 32 is shown in FIG. 3 as a single pole, triple throw switch.

An image processing unit 33 is connected to the outputs of the video image memories 31a, 31b and 31c which reads data out of those memories and processes the data to generate ultrasound B images, which are simultaneously viewable on a monitor 34 connected to the output of the image processing unit 33.

The control unit 30 has an input connected to the output of the signal transmitter 25 which, as stated above, generates signals corresponding to the angular position of the rotor 16.

During operation, as the rotor 16 is rotated, the center axes Aa, Ab and Ac of the transducers 17a, 17b and 17c move in succession through the sector limited by the lines 19a and 19b. The transducer whose center axis is currently within that sector is selected by the control unit 30, which actuates the first switching stage 28 based on the signals identifying the angular position of the rotor 16 supplied to the control unit 30 by the signal transmitter 25. At the same time, the control unit 30 actuates the third switching stage so that the video image memory corresponding to the selected ultrasound transducer is connected to the output of the receiver 27. In the period during which an ultrasound transducer is selected by the first switching stage 28, the control unit 30 actuates the second switching stage 29 rapidly in succession so that the selected ultrasound transducer is alternatingly connected to the transmitter 26 and to the receiver 27. The selected ultrasound transducer may be alternatingly connected to the transmitter 26 and the receiver 27 256 times, for example, during the scanning of a sector-shaped layer. When connected to the transmitter 26, the selected ultrasound transducer generates an ultrasound pulse, and by the time the echo signal corresponding to that pulse has returned to the selected transducer, and is converted into a corresponding electrical signal, the control unit 30 has changed the state of the switching stage 29 so that the electrical signal corresponding to the ultrasound echo is supplied to the receiver 27. This results in a one-to-one relationship between the pulses and the echo signals as is suitable for constructing an ultrasound B-image. The electrical signal corresponding to the ultrasound echo is then supplied to the video image memory corresponding to the selected transducer.

After a complete revolution of the rotor 16, the ultrasound B-images of those sector-shaped layers of the body 4 which were scanned by the ultrasound transducers 17a, 17b and 17c exist in the respective video image memories 31a, 31b and 31c. The images in the memories were acquired in sequence directly after one another, i.e., quasi-simultaneously. The image processing unit 33 reads the data out of the video image memories 31a, 31b and 31c, and displays the corresponding B-images at the same time at the display 34, as indicated by the reference symbols Ba, Bb and Bc. Each of the ultrasound B-images occupies a quadrant on the display 34, with remaining quadrant being available for the display of additional information.

During the next revolution of the rotor 16, the above-described sequence is repeated, with the data from the previous revolution which was stored in the video image memories 31a, 31b and 31c being overwritten with current data. If the ultrasound locating system is operated for the entire treatment duration, it is possible to view even larger displacements of the calculus 14 by the ultrasound B-images on the display 34. If, as shown in FIG. 1, the calculus 14 to be disintegrated is located in the focus zone F of the shock waves, it will be located in the plane which is scannable by the ultrasound transducer 17b, and is visible on the display 34 in the ultrasound B-image Bb. If a displacement of the calculus 14 occurs transversely relative to the center plane 20b of the layer scannable by the transducer 17b, to an extent such that the calculus 14 is no longer within that layer, the calculus 14, depending on the direction of movement, will enter either the layer scannable by the transducer 17a or the layer scannable by the transducer 17c, and accordingly becomes visible either in the image Ba or the image Bc on the display 34. Displacement of the calculus 14 can thus be recognized immediately because the transducers 17a, 17b and 17c scan the respective layers quasi-simultaneously, and the display of the corresponding ultrasound B-images Ba, Bb and Bc on the display 34 ensues at the same time. This provides the possibility of correcting the position of the apparatus and the patient 4 relative to each other immediately upon a displacement of the calculus 14 occurring, so that the calculus 14 is again located in the layer which is scannable by the ultrasound transducer 17b. The position of the focus zone F can be identified on the display 34 by a reticule (not shown in the drawings), thereby assisting in undertaking such re-positioning of the apparatus and/or the body 4 of the patient as is necessary to again locate the calculus 14 in the focus zone F of the shock waves, so that the treatment can be continued.

It should be noted that it is possible to rotate the sector applicator 15 around the acoustic axis A in the directions indicated by the double arrow y to adjust the sector applicator 15 so that the center planes 20a, 20b and 20c of the scannable layers proceed parallel to the primary direction of movement of the calculus 14.

Figure 4:
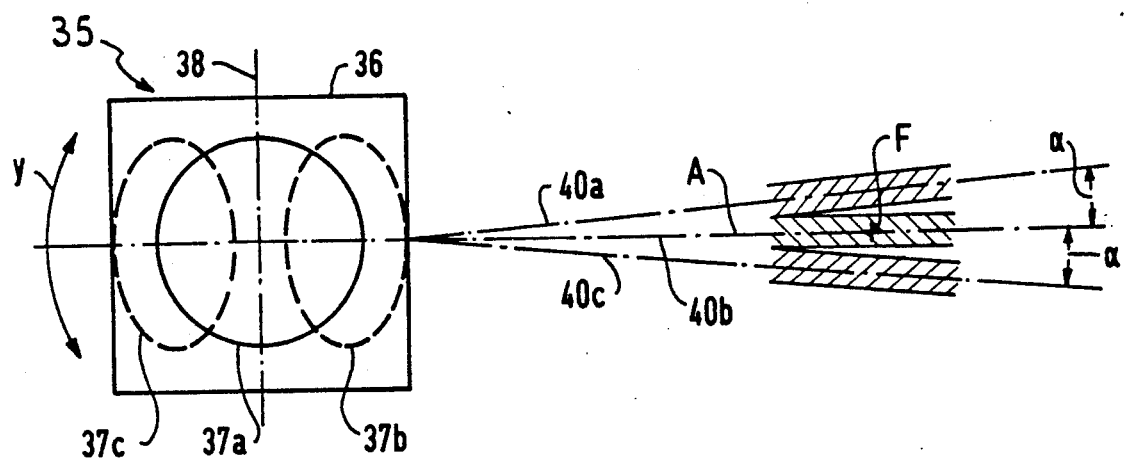
FIG. 4 is a schematic diagram of a further embodiment of an extracorporeal lithotripsy apparatus constructed in accordance with the principles of the present invention for assisting in the description of that further embodiment.

A further embodiment of the ultrasound sector applicator is shown in FIG. 4. This embodiment includes a sector applicator 35 which, except for the mounting described below, operates as described above in connection with FIGS. 1, 2 and 3.

In the embodiment of FIG. 4, the sector applicator 35 is again a mechanical sector scanner and has three ultrasound transducers 37a, 37b and 37c attached to a rotor 36 at angles of 120°. The transducers are arranged on the rotor 36 such that the sector-shaped layers of the body 4 of the patient which are scanned by the respective transducers have respective center planes 40a, 40b and 40c which diverge in the direction toward the focus zone F. The divergency is selected so that those sections of the scannable layers which are located in the area of the focus zone F and are indicated in FIG. 4 by cross-hatching, are directly adjacent to each other. The arrangement is selected so that the center plane 40b of the center layer scannable by the ultrasound transducer 37b contains the acoustic A. The center planes 40a and 40c of the respective layers scannable by the ultrasound transducer 37a and 37c are tilted in opposite directions relative to the acoustic axis A by equal, small angles α. The scannable layers and their respective center planes, 40a, 40b and 40c proceed approximately parallel to each other and approximately parallel to the acoustic axis A, due to the small magnitude of the angle α. It should be noted that, in conjunction with FIG. 4, even though the term "plane" has been used to refer to the center planes 40a, 40b and 40c, this term is only approximately correct for the center planes 40a and 40c. Those surfaces are, more precisely, in the form of an envelope of a cone. In view of the small magnitude of the angle α, however, the portions of those surfaces which are relevant to FIG. 4 sufficiently approximate a plane so that the true, non-planar nature of those surfaces can be neglected.

The embodiment of FIG. 4 is operated by the control circuitry shown in FIG. 3, in the manner already described above, with transducers 37a, 37b and 37c replacing transducers 17a, 17b and 17c which are shown in FIG. 3.

Although modifications and changes may be suggested by those skilled in the art, it is the intention of the inventors to embody within the patent warranted hereon all changes and modifications as reasonable and properly come within the scope of their contribution to the art.

We claim:

1. An extracorporeal lithotripsy apparatus for treating a calculus in a patient, said apparatus comprising:
   means for generating shock waves converging in a focus zone in which a calculus to be disintegrated by successive shock waves from said means for generating shock waves is disposed; and
   ultrasound means for locating said calculus and displaying an image of said calculus including an ultrasound B-scan applicator having a plurality of ultrasound transducers, each ultrasound transducer scanning a different layer, said layers being substantially parallel and having respective sections in the area of said focus zone, said sections being disposed adjacent one another, and means for operating said transducers for quasi-simultaneously scanning said layers during disintegration of said calculus.

2. An apparatus as claimed in claim 1, wherein said means for generating shock waves has an acoustic axis proceeding through said focus zone, and wherein said ultrasound means has an odd number of said ultrasound transducers, including a center ultrasound transducer having a scannable layer therewith which contains said acoustic axis of said means for generating shock waves.

3. An apparatus as claimed in claim 1, wherein each of said different layers respectively scanned by said ultrasound transducers has a center plane, and wherein said respective center planes of said scanned layers are disposed parallel to each other.

4. An apparatus as claimed in claim 1, wherein said means for generating shock waves has an acoustic axis, and said ultrasound B-scan applicator is an ultrasound sector applicator, wherein/each transducer in said ultrasound sector applicator scanning a layer in the shape of a sector, with each scanned sector having a bisector and the bisectors of said different layers being disposed in a common plane with said acoustic axis.

5. An apparatus as claimed in claim 1, wherein said ultrasound B-scan applicator is an ultrasound sector including a rotor on which said plurality of ultrasound transducers are mounted offset at an angle relative to each other, and wherein said ultrasound means further includes means for rotating said rotor around an axis.

6. An apparatus as claimed in claim 5, wherein said means for rotating said rotor is disposed on a side of said means for generating shock waves not facing said focus zone, and said means for rotating including a motor, and a drive element extending through an opening in said means for generating shock waves and providing a drive connection between said rotor and said motor.

7. An apparatus as claimed in claim 5, wherein said ultrasound means includes operating means for said ultrasound transducers for generating ultrasound B-images of each of said different layers and means for simultaneously displaying said ultrasound B-images.

8. An apparatus as claimed in claim 7, wherein said operating means comprises:
transmitter means for driving said ultrasound transducers to generate a B-scan;
receiver means for receiving ultrasound echoes and for converting said ultrasound echoes into corresponding video signals;
a plurality of video image memories, corresponding in number to the plurality of ultrasound transducers, and allocated to said ultrasound transducers on a one-to-one basis;
first switching means for selecting one of said ultrasound transducers;
second switching means for connecting the selected ultrasound transducer to an output of said transmitter means or to an input of said receiver means;
third switching means for connecting an input of one of said video image memories associated with the selected ultrasound transducer to an output of said receiver means;
control means for actuating said first switching means for selecting said ultrasound transducers in succession so that said different layers are successively scanned and for actuating said second switching means for alternatingly connecting the selected ultrasound transducer while scanning the respective layer to said transmitter means and to said receiver means and for actuating said third switching means for connecting the output of said receiver means to the video image memory associated with the selected ultrasound transducer; and
ultrasound image processing unit connected between outputs of said video image memories and said means for displaying for reading data stored in said video image memories and processing said data for generating an ultrasound B-image of each of said different layers and for simultaneously displaying said ultrasound B-images on said means for displaying.

9. An apparatus as claimed in claim 8, further comprising means for transmitting signals to said control means corresponding to the angular position of said rotor so that said control means actuates said first switching means for a time during which the selected ultrasound transducer is in a position for scanning one of said different layers.

10. An extracorporeal lithotripsy apparatus for treating a calculus in a patient, said apparatus comprising:
means for generating shock waves converging in a focus zone in which a calculus to be disintegrated by successive shock waves from said means for generating shock waves is disposed;
an ultrasound applicator having a plurality of ultrasound transducers mounted on a rotor offset relative to each other;
means for rotating said rotor for quasi-simultaneously scanning a plurality of layers by successively moving each of said ultrasound transducers into a position relative to said patient to scan one of said layers, each transducer being mounted on said rotor for scanning a different layer associated with that transducer, said different layers being substantially parallel and having respective sections in the area of said focus zone, said sections being disposed adjacent to each other;
means for generating a signal corresponding to the angular position of said rotor and thereby identifying one of said transducers as being in a position for scanning the layer associated with the transducer;
a plurality of memories corresponding in number to the plurality of said ultrasound transducers and allocated to said ultrasound transducers on a one-to-one basis;
control means connected to said means for generating a signal for alternatingly operating a selected ultrasound transducer currently in said position for scanning to transmit and receive ultrasound signals and for directing the received signals into the memory allocated to the transducer in said position for scanning;
means for generating respective ultrasound B-image from the data respectively stored in said memories; and
means for simultaneously displaying said ultrasound b-images during disintegration of said calculus.

11. An extracorporeal lithotripsy apparatus for treating a calculus in a patient, said apparatus comprising:
means for generating shock waves converging in a focus zone in which a calculus to be disintegrated by successive shock waves from said means for generating shock waves is disposed; and
ultrasound means for locating said calculus and displaying an image of said calculus including an ultrasound B-scan applicator having a plurality of ultrasound transducers, each ultrasound transducer scanning a different layer, each different layer having a center plane and the respective center planes of said layers diverging in the direction of said focus zone and having respective sections disposed adjacent one another in the area of said focus zone, and means for operating said transducers for quasi-simultaneously scanning said layers during disintegration of said calculus.

12. An apparatus as claimed in claim 11, wherein said means for generating shock waves has an acoustic axis proceeding through said focus zone, and wherein said ultrasound means has an odd number of said ultrasound transducers, including a center ultrasound transducer having a scannable layer therewith which contains said acoustic axis of said means for generating shock waves.

13. An apparatus as claimed in claim 11, wherein said means for generating shock waves has an acoustic axis, and wherein said ultrasound B-scan applicator is an ultrasound sector applicator, each transducer in said ultrasound sector applicator scanning a layer in the shape of a sector, with each scanned sector having a bisector and the bisectors of said different layers being disposed in a common plane with said acoustic axis.

14. An apparatus as claimed in claim 13, wherein all but one of said bisectors of said different layers are inclined relative to said acoustic axis.

15. An apparatus as claimed in claim 11, wherein said ultrasound B-scan applicator is an ultrasound sector applicator including a rotor on which said plurality of ultrasound transducers are mounted offset at an angle relative to each other, and wherein said ultrasound means further includes means for rotating said rotor around an axis.

16. An apparatus as claimed in claim 15, wherein said means for rotating said rotor is disposed on a side of said means for generating shock waves not facing said focus zone, and said means for rotating including a motor, and a drive element extending through an opening in said means for generating shock waves and providing a drive connection between said rotor and said motor.

17. An apparatus as claimed in claim 15, wherein said ultrasound means includes operating means for said ultrasound transducers for generating ultrasound B-images of each of said different layers and means for simultaneously displaying said ultrasound B-images.

18. An apparatus as claimed in claim 17, wherein said operating means comprises:
   transmitter means for driving said ultrasound transducers to generate a B-scan;
   receiver means for receiving ultrasound echoes and for converting said ultrasound echoes into corresponding video signals;
   a plurality of video image memories, corresponding in number to the plurality of ultrasound transducers, and allocated to said ultrasound transducers on a one-to-one basis;
   first switching means for selecting one of said ultrasound transducers;
   second switching means for connecting the selected ultrasound transducer to an output of said transmitter means or to an input of said receiver means;
   third switching means for connecting an input of one of said video image memories associated with the selected ultrasound transducer to an output of said receiver means;
   control means for actuating said first switching means for selecting said ultrasound transducers in succession so that said different layers are successively scanned and for actuating said second switching means for alternatingly connecting the selected ultrasound transducer while scanning the respective layer to said transmitter means and to said receiver means and for actuating said third switching means for connecting the output of said receiver means to the video image memory associated with the selected ultrasound transducer; and
   an ultrasound image processing unit connected between outputs of said video image memories and said means for displaying for reading data stored in said video image memories and processing said data for generating an ultrasound B-image of each of said different layers and for simultaneously displaying said ultrasound B-images on said means for displaying.

19. An apparatus as claimed in claim 18, further comprising means for transmitting signals to said control means corresponding to the angular position of said rotor so that said control means actuates said first switching means for a time during which the selected ultrasound transducer is in a position for scanning one of said different layers.

* * * * *